United States Patent [19]
Aristoff

[11] Patent Number: 4,544,764
[45] Date of Patent: Oct. 1, 1985

[54] INTERPHENYLENE CARBACYCLIN COMPOUND

[75] Inventor: Paul A. Aristoff, Portage, Mich.

[73] Assignee: The Upjohn Company, Kalamazoo, Mich.

[21] Appl. No.: 631,977

[22] Filed: Jul. 18, 1984

[30] Foreign Application Priority Data

Jul. 18, 1983 [JP] Japan .......................... 58-111290[U]
Dec. 26, 1983 [JP] Japan .......................... 58-203171[U]

[51] Int. Cl.$^4$ ......................................... C07C 177/00
[52] U.S. Cl. ..................................... 560/56; 562/466
[58] Field of Search .......................... 560/56; 562/466

[56] References Cited

U.S. PATENT DOCUMENTS

| 4,180,657 | 12/1979 | Sih ....................................... 542/426 |
| 4,192,891 | 3/1980 | Haslanger ............................ 424/305 |
| 4,225,508 | 9/1980 | Sih ................................... 260/346.22 |
| 4,238,414 | 12/1980 | Morton, Jr. .......................... 564/453 |
| 4,306,075 | 12/1981 | Aristoff ................................. 560/56 |
| 4,306,076 | 12/1981 | Aristoff ................................. 560/56 |
| 4,486,598 | 12/1984 | Aristoff .............................. 562/466 |

FOREIGN PATENT DOCUMENTS

| 0024943 | 11/1981 | European Pat. Off. .............. 560/56 |
| 2900352 | 7/1979 | Fed. Rep. of Germany . |
| 4024865 | 2/1979 | Japan . |
| 4063059 | 5/1979 | Japan ..................................... 560/56 |
| 4063060 | 5/1979 | Japan ..................................... 560/56 |
| 2012265 | 7/1979 | United Kingdom . |
| 2013661 | 8/1979 | United Kingdom . |
| 2017699 | 10/1979 | United Kingdom . |

OTHER PUBLICATIONS

Aristoff, P. A. et al., "Synthesis and Structure–Activity Relationship of Novel Stable Prostacyclin Analogs," *Advances in Prostaglandin, Thromboxane and Leukotriene Research*, 11, pp. 267–274, 1983.
Aristoff, P. A., "Practical Synthesis of 6a–Carbaprostaglandin I$_2$," *J. Org. Chem.*, 46, pp. 1954–1957, 1981.
Aristoff, P. A., "Synthesis of Benzindene Prostaglandins: A Novel Potent Class of Stable Prostacyclin Analogs," *Tetrahedron Letters*, 23 (20), pp. 2067–2070, 1982.
Barco, Achille et al., "A New, Elegant Route to a Key Intermediate for the Synthesis of 9(O)–Methanoprostacyclin," *J. Org. Chem.*, 45, pp. 4776–4778, 1980.
Kojima, Koichi and Kiyoshi Sakai, "Total Synthesis of 9(O)–Methanoprostacyclin and Its Isomers," *Tetrahedron Letters*, 39, pp. 3743–3746, 1978.
Konishi, Toshitaka et al., "A Synthesis of 9(O)–Methanoprostacyclin," *Chemistry Letters*, pp. 1437–1440, 1979.
Morton, Douglas R., Jr. and Frances C. Brokaw, "Total Synthesis of 6a–Carbaprostaglandin I$_2$ and Related Isomers," *J. Org. Chem.* 44 (16), pp. 2880–2887, 1979.
Nicolaou, Kyriacos C. et al., "Total Synthesis of Carboprostacyclin, a Stable and Biologically Active Analogue of Prostacyclin (PGI$_2$)," *J.C.S. Chem. Comm.*, pp. 1067–1068, 1978.
Shibasaki, Masakatsu et al., "A Stereo and Regiospecific Route to the Synthetic Intermediate for the Synthesis of 9(O)–Methanoprostacyclin," *Chemistry Letters*, pp. 1299–1300, 1979.
Shibasaki et al., "New Synthetic Routes to 9(O)–Methanoprostacyclin, A Highly Stable and Biologically Potent Analog of Prostacyclin," *Tetrahedron Letters*, 5, pp. 433–436, 1979.
Skuballa, VonWerner and Helmut Vorbruggen, "Ein neuer Weg zu 6a–Carbacyclinen–Synthese eines stabilen, biologisch potenten Prostacyclin–Analogons," *Angew. Chem.*, 93, pp. 1080–1081, 1981.
Sugie, Akihiko et al., "Stereocontrolled Approaches to 9(O)–Methanoprostacyclin," *Tetrahedron Letters*, 28, pp. 2607–2610, 1979.
Yamazaki, Mayumi, "1,2-Carbonyl Transposition of cis–Bicyclo[3.3.0]octan-2-one to Its 3-One Skeleton: Application to Syntheses of dl–Hirsutic Acid and dl-9-(O)–Methanoprostacyclin," *Chemistry Letters*, pp. 1245–1248, 1981.

*Primary Examiner*—Paul J. Killos
*Attorney, Agent, or Firm*—L. Ruth Hattan

[57] ABSTRACT

The compound 15-cyclohexyl-9-deoxy-13,14-dihydro-2',9α-methano-3-oxa-4,5,6,16,17,18,19,20-octanor-3,7(1',3-interphenylene)PGF$_1$ and pharmacologically acceptable salts thereof.

1 Claim, No Drawings

INTERPHENYLENE CARBACYCLIN COMPOUND

FIELD OF INVENTION

The present invention relates to an interphenylene carbacyclin compound and pharmacologically useful salts thereof.

PRIOR ART

The compound and salts thereof of the present invention are generically disclosed in U.S. Pat. No. 4,306,075, issued Dec. 15, 1981. Related interphenylene carbacyclins are described and claimed in U.S. Pat. Nos. 4,306,075, 4,306,076, and EP 87237 (Derwent No. 754477). Compounds having a 5-membered oxa ring are described in European Pat. No. 24-943 (Derwent No. 19801D).

Carbacyclin and closely related compounds are known in the art. See Japanese Kokai 63,059 and 63,060, also abstracted respectively as Derwent Farmdoc CPI Numbers 48154B/26 and 48155B/26. See also British published specifications Nos. 2,012,265 and German Offenlungsschrift No. 2,900,352, abstracted as Derwent Farmdoc CPI Number 54825B/30. See also British published applications Nos. 2,017,699 and 2,013,661 and U.S. Pat. No. 4,238,414.

The synthesis of carbacyclin and related compounds is also reported in the chemical literature, as follows: Morton, D. R., et al, J. Org. Chem., 44:2880–2887 (1979); Shibasaki, M., et al, Tetrahedron Lett., 433–436 (1979); Kojima, K., et al, Tetrahedron Lett., 3743–3746 (1978); Nicolaou, K. C., et al, J. Chem. Soc., Chemical Communications, 1067–1068 (1978); Sugie, A., et al, Tetrahedron Lett., 2607–2610 (1979); Shibasaki, M., Chem. Lett., 1299–1300 (1979), and Hayashi, M., Chem. Lett., 1437–40 (1979); Aristoff, P. A., J. Org. Chem. 46, 1954–1957(1981); Yamazaki, M., et al, Chem. Lett., 1245–1248(1981); and Barco, A., et al, J. Org. Chem. 45, 4776–4778 (1980); and Skuballa, W., et al, Angew. Chem. 93, 1080–1081 (1981). The utility and synthesis of compounds closely related to those claimed herein is described in Aristoff, P. A., and Harrison, A. W., Tetrahedron Lett. 23, 2067–2070 (1982) and in Advances in Prostaglandin, Thromboxane, and Leukotriene Research, Vol. 11, 267 (1983).

7-Oxo and 7-hydroxy-CBA$_2$ compounds are apparently disclosed in U.S. Pat. No. 4,192,891. 19-Hydroxy-CBA$_2$ compounds are disclosed in U.S. Pat. No. 4,225,508. CBA$_2$ aromatic esters are disclosed in U.S. Pat. No. 4,180,657. 11-Deoxy-$\Delta^{10}$- or $\Delta^{11}$-CBA$_2$ compounds are described in Japanese Kokai 77/24,865, published 24 Feb. 1979.

SUMMARY OF INVENTION

The invention is 15-cyclohexyl-9-deoxy-13,14-dihydro-2',9α-methano-3-oxa-4,5,6,16,17,18,19,20-octanor-3,7-(1',3-interphenylene)PGF$_1$, having the structure depicted in Formula III, and pharmacologically acceptable salts thereof. The compound of this invention has been found to have unexpectedly superior properties as an antisecretory cytoprotective agent.

DETAILED DESCRIPTION OF INVENTION

The compound of the present invention is prepared by the reaction of the compounds of Formulas I and II as described in Example 3 hereof. Examples 1 and 2 describe the synthesis of the starting materials of Formulas I and II, respectively.

Pharmacologically acceptable salts of the compound of Formula III are those with pharmacologically acceptable metal cations, ammonia, amine cations or quaternary ammonium cations. Illustrative metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium and phenyltriethylammonium.

It has been found that the compound of the present invention and pharmacologically acceptable salts thereof have unexpectedly superior antisecretory/cytoprotective properties. The compound and salts thereof of the present invention are useful as antisecretory and cytoprotective agents orally in warm blooded animals, such as rats, monkeys, dogs, horses, cows, cats and humans when administered at a dosage of from 0.1 to 100 μg/kg of animal body weight 1 to 4 times per day. The preferred dosage for humans in from 0.1 to 1.5 μg/kg of body weight 1 to 4 times per day. The dosages set forth herein are applicable to both antisecretory and cytoprotective activities or functions. Generally in compounds having both antisecretory and cytoprotective activities the effective doses of compound to achieve either maximum antisecretory or maximum cytoprotective effectiveness are quite different. Thus the compound and salts thereof of the present invention are unique in that they are effective at a markedly low dosage range and additionally are effective as antisecretory as well as cytoprotective agents at substantially the same dosage range.

Administration of the compound and salts thereof of the present invention by the oral route is preferred. However, there may be circumstances under which intravenous or subcutaneous administration is necessary or preferred in which case significantly reduced amounts of compound will be administered depending upon the patient, i.e., warm blooded animal, being treated and the condition of same.

The utility of 15-cyclohexyl-9-deoxy-13,14-dihydro-2',9α-methano-3-oxa-4,5,6,16,17,18,19,20-octanor-3,7-(1',3-interphenylene)-PGF$_1$ as an antisecretory and cytoprotective agent was demonstrated in the gastric cytoprotective, the intestinal cytoprotective, and the gastric antisecretory tests described hereinbelow. The results set forth the ED$_{50}$ for 15-cyclohexyl-9-deoxy-13,14-dihydro-2',9α-methano-3-oxa-4,5,6,16,17,18,19,20-octanor-3,7-(1',3-interphenylene)-PGF$_1$ as well as for 9-deoxy-13,14-dihydro-2',9α-methano-3-oxa-4,5,6-trinor-3,7-(1',3'-interphenylene)-PGF$_1$, and 16,16-dimethyl-PGE$_2$.

Gastric Cytoprotection. Female rats (derived from the Sprague-Dawley strain) of 205–220 g were fasted for 24 hours. During the last 18 hours they were placed in individual semi-restraining cages to prevent coprophagy. Water was also withheld during the overnight period. On the following morning, 15-cyclohexyl-9-deoxy-13,14-dihydro-2',9α-methano-3-oxa-4,5,6,16,17,18,19,20-octanor-3,7-(1',3-interphenylene)-PGF$_1$; 9-deoxy-13,14-dihydro-2',9α-methano-3-oxa-4,5,6-trinor-3,7-(1',3'-interphenylene)-PGF$_1$; or 16,16-dimethyl-PGE$_2$ were administered orally, 30 minutes before oral administration of 1 ml of absolute ethanol. Each compound was given at various dose levels (from 0.01 to 150 μg/kg). One hour after absolute ethanol administration the animals were killed with CO$_2$, their stomachs were dissected out, opened along the greater curvature, rinsed with tap water, and randomized so that the examiner was unaware of the treatment given. They were examined with a 2× binocular magnifier for the presence of gastric mucosal necrotic lesions. The average number of lesions per stomach in each group was calculated, and the results were expressed as ED$_{50}$, i.e., dose reducing by 50% the average number of gastric lesions. The number of gastric lesions is inversely related to the cytoprotective activity of a given compound. Five to 15 rats per group were used.

Results: The ED$_{50}$, in μg/kg, for each compound is the following:

15-Cyclohexyl-9-deoxy-13,14-dihydro-2',9α-methano-3-oxa-4,5,6,16,17,18,19,20-octanor-3,7-(1',3-interphenylene)-PGF$_1$: 1.

9-Deoxy-13,14-dihydro-2',9α-methano-3-oxa-4,5,6-trinor-3,7-(1',3'-interphenylene)-PGF$_1$: 7.

16,16-Dimethyl-PGE$_2$: 0.025.

Intestinal Cytoprotection. Female rats of 205–215 g were used, being fed ad libitum throughout the experiment. Indomethacin was given orally at a dose of 15 mg/kg in 1 ml of water containing Tween80 (1 drop per 20 ml) as suspending agent. The suspension was prepared in a glass homogenizer on the day of the experiment.

Indomethacin was given only once, on the first day of the experiment. 15-Cyclohexyl-9-deoxy-13,14-dihydro-2',9α-methano-3-oxa-4,5,6,16,17,18,19,20-octanor-3,7-(1',3-interphenylene)-PGF$_1$; 9-deoxy-13,14-dihydro-2',9α-methano-3-oxa-4,5,6-trinor-3,7-(1',3'-interphenylene)-PGF$_1$; or 16,16-dimethyl-PGE$_2$ were administered orally twice a day (7:15 a.m.–3:15 p.m.) at various dose levels (from 1.5 to 3000 μg/kg) for three days. The first treatment was given 30 minutes before indomethacin. After three days of treatment, the animals were killed with CO$_2$. After randomization of the animals the small intestine was examined for the presence of lesions characterized by (a) palpable nodules on the mesenteric side of the jejunum and the ileum; (b) multiple ulcers throughout these two intestinal segments; and (c) adhesions of intestinal loops caused by perforation of these ulcers. The percent of animals showing any one of these three lesions was recorded. The results were expressed as ED$_{50}$, i.e., dose reducing by 50% the incidence of animals with intestinal lesions. Three to 14 rats per group were used.

Results: The ED$_{50}$, in μg/kg, for each compound is the following:

15-Cyclohexyl-9-deoxy-13,14-dihydro-2',9α-methano-3-oxa-4,5,6,16,17,18,19,20-octanor-3,7-(1',3-interphenylene)-PGF$_1$: 25.

9-Deoxy-13,14-dihydro-2',9α-methano-3-oxa-4,5,6-trinor-3,7-(1',3'-interphenylene)-PGF$_1$: 4000.

16,16-Dimethyl-PGE$_2$: 25.

Gastric Antisecretory Activity: Pylorus ligated female rats weighing 205–215 g were fasted according to the same procedure described for the gastric cytoprotection studies. On the following morning the pylorus was ligated under ether anesthesia (Shay rat preparation). 15-Cyclohexyl-9-deoxy-13,14-dihydro-2',9α-methano-3-oxa-4,5,6,16,17,18,19,20-octanor-3,7-(1',3-interphenylene)-PGF$_1$; 9-deoxy-13,14-dihydro-2',9α-methano-3-oxa-4,5,6-trinor-3,7-(1',3'-interphenylene)-PGF$_1$; or 16,16-dimethyl-PGE$_2$ were administered orally at various dose levels (from 0.01 to 15 mg/kg), one hour before pylorus ligation.

Immediately after pylorus ligation, 10 ml of saline was injected subcutaneously to compensate for dehydration that may have occurred during the fasting period. The animals were killed with CO$_2$ three hours after pylorus ligation. The esophagus was clamped, the stomach was dissected out and its contents emptied into a graduated test tube. The volume was read to the nearest 0.1 ml. Aliquots of gastric juice were taken for determination of acid content. Acidity was determined by titration with 0.1M NaOH, using an automatic titrator (Copenhagen radiometer), and was expressed as mEq/three hours (output). The results were expressed as ED$_{50}$, i.e., dose reducing acid output by 50%. Five to 15 animals were used per group.

Results: The ED$_{50}$, in μg/kg, for each compound is the following:

15-Cyclohexyl-9-deoxy-13,14-dihydro-2',9α-methano-3-oxa-4,5,6,16,17,18,19,20-octanor-3,7-(1',3-interphenylene)-PGF$_1$: 30.

9-Deoxy-13,14-dihydro-2',9α-methano-3-oxa-4,5,6-trinor-3,7-(1',3'-interphenylene)-PGF$_1$: 4000.

16,16-Dimethyl-PGE$_2$: 250.

The compound and its pharmacologically acceptable salts of the present invention can be formulated for administration to the patient to be treated by conventional means to form tablets, pills, capsules, elixirs or other conventional solid or liquid unit dosage forms which generally will contain the suitable carriers, lubricants, fillers, disintegrating agents or other standard formulation components by procedures well known in the art.

The following specific examples illustrate the preparation of 15-cyclohexyl-9-deoxy-13,14-dihydro-2',9α-methano-3-oxa-4,5,6,16,17,18,19,20-octanor-3,7-(1',3-interphenylene)-PGF$_1$ which can be converted to pharmacologically acceptable salts by means known in the art, for example, as described in U.S. Pat. No. 4,306,075.

EXAMPLE 1

2,3,3A-4-Tetrahydro-5-methoxy-2-oxo-naphtho[2,3-B]furan (Formula I)

(a)

3,4-Dihydro-2-hydroxy-5-methoxynaphthalenecarboxylic acid methyl ester

A solution of 5-methoxy-β-tetralone (20.6 g, 117 mmol) and 350 ml of dimethylcarbonate was cooled to 0° to 5° C., then treated with 32 ml (140 mmol) of 25% sodium methoxide in oxygen-free methanol. The resulting dark brown solution was stirred for 30 minutes at 0° C., then heated to 70° C., stirred for 18 hours under a nitrogen atmosphere, then cooled to 0° to 5° C. and quenched with 200 ml of cold 1N degassed aqueous hydrochloric acid. The solution was extracted with ethyl acetate (2×150 ml). The combined organic layers were washed with brine (2×200 ml), dried over magnesium sulfate, filtered, and rotary evaporated at 50° C. The resulting red-brown oil was crystallized from 80 ml of 1:1 ether/hexane in the freezer to give 14.43 g (53%) of yellow crystals, m.p. 56°–58° C. A second crop of yellow crystals (3.6 g, 14%) can be obtained from 20 ml 1:1 ether/hexane, m.p. 55°–58° C. The mother liquor (~12 g) was chromatographed on 100 g of silica gel 60 slurry packed in 300 ml of hexane. Eluting with 2% ethyl acetate in hexane gave 5.1 g (19%) of the title compound (a) in fractions 17–28, m.p. 53°–58° C. Total yield of compound (a) was 23.1 g (85%).

NMR (CDCl$_3$, TMS): δ 2.3–2.7 (m, 2H), 2.8–3.0 (m, 2H), 3.80 (s, 3H), 3.90 (s, 3H), 6.6–7.5 (m, 3H), 13.35 (s, 1H).

Infrared: $\nu_{max}$ (mull): 1640, 1598, 1587, 1566, 1422, 1378, 1311, 1277, 1220, 1207, 1086, 1052, 1030, 892, 787, 769, 721 cm$^{-1}$.

TLC (silica Gel GF): Rf=0.47 in 10% ethyl acetate in hexane.

(b)

3,4-Dihydro-2-hydroxy-3-(3-propene)-5-methoxynaphthalenecarboxylic acid methyl ester A solution of 300 ml of tetrahydrofuran and 39 ml (282 mmol) of diisopropylamine under nitrogen, was cooled to −50° C. and treated with 170 ml (272 mmol) of 1.6M n-butyllithium in hexane dropwise maintaining the temperature at −50° C. The solution was stirred at −50° C. for 15 minutes, then at 0° C. for 15 minutes. A solution of 30.0 g (128.1 mmol) of 3,4-dihydro-2-hydroxy-5-methoxynaphthalenecarboxylic acid methyl ester in 70 ml of tetrahydrofuran was added dropwise to maintain the temperature at 0° C. The resulting yellow suspension was treated with 13.5 ml (160 mmol) of allyl bromide in 50 ml of tetrahydrofuran dropwise maintaining the temperature at 0° C. The cooling bath was removed and the orange solution was stirred at ambient temperature for 1 hour, then cooled to 10° to 15° C. and 500 ml of 1N degassed aqueous hydrochloric acid was added dropwise maintaining the temperature below 15° C. The layers were separated and the aqueous layer extracted with 400 ml of ethyl acetate. The organic layers were combined and washed with 500 ml of brine, dried over anhydrous magnesium sulfate, filtered and concentrated via rotary evaporation and then house vacuum to give 44.2 g of the title compound (b), m.p. 70°–71° C.

NMR (CDCl$_3$, TMS): δ 1.8–3.2 (m, 5H), (3H singlets at 3.80 δ and 3.90 δ; 6H) 4.7–5.4 (m, 2H), 5.5–6.1 (m, 1H), 6.5–7.6 (m, 3H), 13.4 (s, 1H).

Infrared: $\nu_{max}$ 2925, 2956, 1237, 1598, 1440, 1270, 1257, 1051, 1002, 885, 790, 772 cm$^{-1}$. TLC (Silica Gel GF): Rf=0.34 in 10% ethyl acetate in hexane.

(c)

1,2,3,4-Tetrahydro-5-methoxy-3-(3-propene)naphthalen-2-one

A mixture of 44.1 g of 3,4-dihydro-2-hydroxy-5-methoxy-3-(3-propene)naphthalenecarboxylic acid methyl ester and 110 ml of dimethyl sulfoxide was degassed with nitrogen and heated to ~50° C. under nitrogen to effect dissolution. The resulting orange solution was treated with 6.0 g (142 mmol) of anhydrous lithium chloride and 7.5 ml of deionized water and heated to 150° C. under nitrogen, then stirred at 150° C. for 4 hours. The solution was cooled to 10° to 15° C., diluted with 500 ml of 1:1 brine/water and extracted with three 200 ml portions of ethyl acetate. The organic layers were combined and washed with three 200 ml portions of water, two 200 ml portions of brine, dried over anhydrous magnesium sulfate, filtered and concentrated in vacuo to give 28.3 g of the title compound (c), m.p. 39°–40° C.

NMR (CDCl$_3$, TMS): δ 1.8–2.8 (m, 4H), 3.0–4.3 (m, including 2H broad singlet at 3.53 δ and 3H singlet at 3.80 δ, 6H), 4.8–5.4 (m, 2H), 5.5–6.1 (m, 1H), 6.5–7.4 (m, 3H).

Infrared: $\nu_{max}$ 2922, 1713, 1642, 1599, 1588, 1472, 1441, 1436, 1258, 1081, 910, 771, 719, 609 cm$^{-1}$. TLC (Silica Gel GF): Rf=0.32 in 10% elthyl acetate in hexane.

(d) The 2-ethylenedioxy ketal of 1,2,3,4-tetrahydro-5-methoxy-3-(3-propene)naphthalen-2-one A solution of 27.8 g (128 mmol) of 1,2,3,4-tetrahydro-5-methoxy-3-(3-propene)naphthalen-2-one, 450 ml of methylene chloride, 150 ml (2.2 mmol) of ethylene glycol, 60 ml (450 mmol) of triethylorthoformate, and 270 mg (1.41 mmol) of p-toluenesulfonic acid monohydrate was degassed with nitrogen and stirred at room temperature under nitrogen for 22 hours after which the reaction was quenched with 7.5 ml (52 mmol) of triethylamine, diluted with 500 ml of 1:1 saturated aqueous sodium bicarbonate/water and the layers were separated. The aqueous layer was extracted with 200 ml of methylene chloride. The combined organic layers were washed with three 500 ml portions of water and 500 ml of brine, then concentrated by rotary evaporation to give ~40 g of a red oil. The red oil was dissolved in 200 ml of hexane and treated with 200 ml of water. The mixture was degassed and stirred under nitrogen for one hour. The layers were separated and the organic layer was dried with anhydrous magnesium sulfate, then filtered and concentrated in vacuo to give ~35 g of orange oil. The orange oil was filtered through 100 g of silica gel 50 washing with 800 ml of 10% ethyl acetate in hexane. The filtrate was concentrated in vacuo to give 31.5 g (94%) of the title compound (d), m.p. 34°–35° C.

NMR (CDCl$_3$, TMS)" δ 1.7–3.3 (m, including 2H broad singlet at 2.90 δ, 7H), 3.4–4.4 (m, including 3H singlet at 3.77 δ, 7H), 4.8–5.3 (m, 2H), 5.6–6.2 (m, 1H), 6.5–7.4 (m, 3H).

Infrared: $\nu_{max}$ (film): 2940, 2890, 1620, 1590, 1470, 1440, 1260, 1155, 1075, 950, 770 cm$^{-1}$. TLC (Silica Gel GF): RF=0.35 in 10% ethyl acetate in hexane.

(e)
2,2-Ethylenedioxy-5-methoxy-1,2,3,4-tetrahydro-naphthalen-3-ylacetic acid To a mixture of 1400 ml of deionized water and 66.5 g (310 mmol) of sodium metaperiodate was added 1.0 g (6.4 mmol) of potassium permanganate. The purple solution was stirred for 30 minutes at room temperature then treated in sequence with 5.0 g (36 mmol) of anhydrous potassium carbonate, then 350 ml of t-butanol, followed by 8.9 g (34 mmol) of ethylenedioxy ketal of 1,2,3,4-tetrahydro-5-methoxy-3-(3-propene)naphthalen-2-one in 350 ml of t-butanol. The resulting reddish-purple suspension was stirred at room temperature for 2 hours. The reaction was quenched with 10 ml (150 mmol) of ethylene glycol and stored at room temperature for 2.5 hours. Approximately 30% of the solvent was removed via rotary evaporation, and the remaining material was acidified to pH 3-4 with 100 ml of 1M aqueous hydrochloric acid and extracted with three 500 ml portions of ethyl acetate. The organic layers were combined and washed with two 500 ml portions of brine, dried over anhydrous sodium sulfate, filtered, and the solvents removed in vacuo to give 8.5 g (89%) of the title compound (e), m.p. 129°-130° C.

Infrared: $\nu_{max}$ 2927, 1703, 1587, 1471, 1266, 1143, 1082, 1059, 948, 873, 765 cm$^{-1}$.

NMR (CDCl$_3$, TMS): δ 1.8-3.4 (m, 6H), 3.9-4.5 (m, including 3H singlet at 3.77 δ, 8H), 6.4-7.4 (m, 3H), 10.27 (broad singlet, 1H). TLC (Silica Gel GF): Rf=0.20 in 30% ethyl acetate in hexane.

(f)
5-Methoxy-2-oxo-1,2,3,4-tetrahydronaphthalen-3-ylacetic acid

A solution of 8.0 g (28.7 mmol) of 2,2-ethylenedioxy-5-methoxy-1,2,3,4-tetrahydronaphthalen-3-ylacetic acid, 80 ml of 3N aqueous hydrochloric acid, and 80 ml of acetone was degassed and heated to 60° C. under nitrogen then stirred under nitrogen at 60° C. for 4 hours. The reaction was cooled to room temperature, approximately 50% of the solvent was removed by rotary evaporation, diluted with 100 ml of brine, and extracted with three 100 ml portions of ethyl acetate. The organic layers were combined and washed with two 100 ml portions of brine, dried over anhydrous sodium sulfate, filtered, and concentrated via rotary evaporation to give an orange solid. The orange solid was triturated with 10 ml of ether and filtered to give 4.9 g (73%) of the title compound (f), m.p. 129°-131° C.

NMR (CDCl$_3$, TMS): δ 2.2-3.2 (m, 4H), 3.3-4.0 (m, including 2H broad singlet at 3.67 δ and 3H singlet at 3.85 δ, 6H), 6.4-6.9 (m, 2H), 7.1-7.3 (m, 1H), 10.2 (bs, 1H).

Infrared: $\nu_{max}$ 2908, 2855, 1730, 1714, 1676, 1471, 1454, 1446, 1266, 1202, 1195, 1184, 1091, 776, 747, 724 cm$^{-1}$.

TLC (Silica Gel GF): Rf=0.22 in 35% ethyl acetate in hexane with 1% acetic acid.

(g)
2,3,3A,4-Tetrahydro-5-methoxy-2-oxo-naphtho[2,3-B]furan

A solution of 5-methoxy-2-oxo-1,2,3,4-tetrahydronaphthalen-3-yl-acetic acid (1.75 g, 7.49 mmol) in 88 ml of ethyl acetate was treated all at once with 88 ml of a reagent prepared immediately before use as follows: 20.0 ml of a solution of 0.40 ml of 70% perchloric acid in 100 ml of ethyl acetate was added to 50 ml of ethyl acetate, then 19.2 ml (0.20 mmol) of acetic anhydride was added and the reagent diluted to a total volume of 100 ml with ethyl acetate. The solution was stirred for 10 minutes at room temperature under nitrogen then quenched with 100 ml of saturated aqueous sodium bicarbonate. The layers were separated and the organic layer was washed with 100 ml of brine, dried with anhydrous sodium sulfate, filtered and concentrated in vacuo. To remove the excess acetic anhydride, the red oil was treated with 10 drops of pyridine and 200 ml of methanol. The solvents were removed in vacuo (rotovap bath below 30° C.); then to remove the pyridine 100 ml of toluene was added and the solvents were removed in vacuo (rotovap bath below 35° C.). An additional 100 ml of toluene was added and concentrated in vacuo to give a yellow solid. The yellow solid was recrystallized from ethyl acetate and hexane to give 890 mg (55%) of the title compound (g) as a white solid, m.p. 139°-141° C.

NMR (CDCl$_3$, TMS): δ 2.0-4.1 (m, including 3H singlet at 3.86 δ, 8H), 6.0-6.2 (d, J=3 Hz, 1H), 6.6-7.0 (m, 2H), 7.0-7.4 (m, 1H).

Infrared: $\nu_{max}$ 2926, 1800, 1686, 1571, 1472, 1444, 1267, 1075, 964, 865, 850, 780 cm$^{-1}$.

CMR (CDCl$_3$, TMS): δ ppm (relative intensity): 173.94 (14), 156.31 (17), 154.89 (18), 134.98 (17), 127.79 (92), 121.42 (11), 119.48 (90), 109.60 (97), 101.09 (81), 55.48 (64), 34.76 (88), 33.17 (88), 27.29 (85).

UV: 218 nm (ε=17,650), 267 nm (ε=7,150), 293 nm (sh, ε=2,000), 303 nm (sh, ε=1,150). TLC (Silica Gel GF): Rf=0.32 in 15% ethyl acetate in hexane.

EXAMPLE 2

Dimethyl[(4R)-4-cyclohexyl-4-tetrahydropyran-2-yloxybutyl]phosphonate (Formula II wherein alkylO is CH$_3$O and Rx is tetrahydropyranyl)

(a) 1-Cyclohexylprop-2-enol

To 140 ml of dry tetrahydrofuran, degassed and flushed with nitrogen (3×) and cooled to 0° C. under nitrogen, was added 1.3M vinyl magnesium bromide (195 ml, 253.5 mmol) in tetrahydrofuran rapidly and dropwise over 5 minutes. The resulting solution was stirred for 5 minutes at 0° C. under nitrogen after which a solution of 24.0 g (223 mmol) of cyclohexylcarboxaldehyde in 40 ml of dry tetrahydrofuran was added via syringe at 0° C. The resulting mixture was stirred for 3.75 hours at 0° to 5° C. under a nitrogen atmosphere after which the reaction was quenched at 0° C. by careful addition of saturated aqueous ammonium chloride. The resulting suspension was poured into 1 L of ice cold, saturated, aqueous ammonium chloride and extracted with ethyl acetate. The ethyl acetate extracts were combined and washed with saturated aqueous ammonium chloride, saturated aqueous sodium bicarbonate, then with brine. The ethyl acetate extract was dried over magnesium sulfate, filtered, and concentrated at room temperature to give 31.0 g of 1-cyclohexyl-prop-2-enol.

NMR (CDCl$_3$, TMS): δ 0.73-2.67 (m, 12H), 3.87 (t, J=6 Hz, 1H), 5.07-5.43 (m, 2H), 5.67-6.13 (m, 1H).

Infrared (film): 3370, 2925, 1450, 1020, 990, 975, 890 cm$^{-1}$. TLC (Silica Gel GF): Rf=0.54 in 25% ethyl acetate in hexane.

(b) (R)-1-Cyclohexyl-prop-2-enol

To 2.2 L of methylene chloride, degassed and flushed with nitrogen and cooled to −25° C. under nitrogen, was added 72.2 ml of titanium tetraisopropoxide (242.5 mmol) at −25° C. The solution was stirred for 5 minutes at −25° C. after which 62.16 ml of (−)-diisopropyl(D)tartrate (290 mmol) was added at −25° C. under nitrogen. A solution of 31.0 g (214 mmol) of 1-cyclohexylprop-2-enol in 50 ml of methylene chloride was added to the reaction mixture at −25° C. The resulting solution was stirred for 10 minutes at −25° C. under nitrogen after which 3M t-butylhydroperoxide in dichloroethane (48.5 ml, 145.5 mmol) was added at −25° C. The mixture was stirred for 10 minutes at −25° C., then stirred for 3 days at −20° C. The reaction was quenched by cannulating the reaction mixture (at −20° C.) into a mechanically stirred tartaric acid-ferrous sulfate solution (200 g/400 g in 2 L water) at 0° C. The resulting suspension was stirred at 0° C. for 30 minutes and filtered through a pad of celite, washing the pad thoroughly with methylene chloride. The filtrate layers were separated and the aqueous layer was extracted with methylene chloride. The organic extracts were combined and washed with brine, dried over magnesium sulfate, filtered and concentrated at room temperature via rotovap to give the title compound 2(b) as a yellow oil which was purified as follows: The oil was dissolved in 650 ml of hexane and cooled to 0° C. under nitrogen then treated with aqueous 1N sodium hydroxide (550 ml) at 0° C. The resulting suspension was stirred for 40 minutes at 0° C. after which the layers were separated and the aqueous layer was extracted with hexane. The organic extracts were combined, washed with brine, dried over sodium sulfate, filtered and concentrated at room temperature via rotovap to a yellow oil. The yellow oil was chromatographed on silica gel packed with 12% ethyl acetate in Skellysolve B (SSB) eluting with 12% in SSB to give 9.59 g of the title compound 2(b).

NMR (CDCl$_3$, TMS): δ 0.73–2.67 (m, 12H), 3.87 (t, 1H, J=6 Hz), 5.07–5.43 (m, 2H), 5.67–6.13 (m, 1H).

Infrared (film): 3370, 2925, 1450, 1020, 990, 975, 890 cm$^{-1}$. TLC (Silica Gel GF): Rf=0.54 in 25% ethyl acetate in hexane.

(c) 3-Cyclohexyl-3-tetrahydropyranyloxy-prop-1-ene

A solution of 22.07 g of (R)-1-cyclohexyl-prop-2-enol in 300 ml of methylene chloride, degassed and flushed with nitrogen, was treated at ambient temperature with pyridinehydrochloride (0.145 g) and then with dihydropyran (44.4 ml, 466 mmol). The reaction mixture was stirred overnight at ambient temperature under nitrogen, then cooled using an ice bath and treated with aqueous sodium bicarbonate (15 ml). The resulting solution was diluted with saturated aqueous sodium bicarbonate (200 ml), stirred for 5 minutes after which the layers were permitted to separate. The organic layer was washed with brine, dried over anhydrous sodium sulfate, filtered and the filtrate concentrated to give 35.0 g of compound 2(c) as a yellow oil.

NMR (CDCl$_3$, TMS): δ 0.63–2.20 (m, 17H), 3.27–4.10 (m, 3H), 4.67 (bs, 1H), 4.93–5.33 (m, 2H), 5.40–6.13 (m, 1H).

Infrared (film): 2925, 2855, 1130, 1115, 1080, 1035, 1020, 1015, 995, 980 cm$^{-1}$.

TLC (Silica Gel GF): Rf=0.62 in 25% ethyl acetate in hexane.

(d) 3-Cyclohexyl-3-tetrahydropyranyloxy-propanol

A solution of 35.0 g of 3-cyclohexyl-3-tetrahydropyranol-prop-1-ene (157 mmol) in 795 ml of dry tetrahydrofuran, degassed and flushed with nitrogen, then cooled to 0° C., was treated dropwise at 0° C. with 0.5M 9-BBN (9-borabicyclononane) in tetrahydrofuran (795 ml, 398 mmol). The resulting solution was stirred for one hour at 0° C. after which the cooling bath was removed and stirring was continued at ambient temperature for 6 hours. The reaction mixture was then cooled to 0° C. and treated slowly with 30% hydrogen peroxide (231 ml), then treated with 3N potassium hydroxide (231 ml) all at once. The resulting suspension was stirred for 35 minutes at 0° C. after which the cooling bath was removed and the reaction suspension was stirred for one hour at ambient temperature. The reaction mixture was then diluted with brine, the layers separated, and the aqueous layer was extracted with ethyl acetate. The organic layers were combined and washed with brine, dried over anhydrous sodium sulfate, filtered, and the filtrate concentrated in vacuo. The resulting product was chromatographed on silica gel eluting with ethyl acetate in SSB to give 27.19 g of compound 2(d).

NMR (CDCl$_3$, TMS): δ 0.63–2.90 (m, 20H), 3.23–4.13 (m, 5H), 4.03–4.87 (m, 1H).

Infrared (film): 3435, 2930, 2855, 1450, 1160, 1135, 1075, 1025, 990 cm$^{-1}$. TLC (Silica Gel GF): Rf=0.21–0.38 in 30% ethyl acetate in hexane.

(e) The 1-p-toluenesulfonyl derivative of 3-cyclohexyl-3-tetrahydropyranyloxy-propanol A solution of 27.19 g (112 mmol) of 3-cyclohexyl-3-tetrahydropranyloxypropanol in 136 ml of dry pyridine cooled to 0° C. was treated with 25.7 g (135 mmol) of p-toluenesulfonyl chloride. The reaction mixture was stirred for 20 hours at 0° C. under nitrogen after which 350 g of ice was added and the cooling bath was removed. The reaction mixture was stirred for 75 minutes, then diluted with water, and extracted with ethyl acetate. The organic layers were combined, washed with saturated aqueous sodium bicarbonate, water, and brine, and dried over anhydrous sodium sulfate, filtered, and the filtrate concentrated at room temperature. The residual pyridine was removed azeotropically using toluene to give 38.09 g of compound 2(e).

NMR (CDCl$_3$, TMS): δ 0.63–2.20 (m, 19H), 2.47 (s, 3H), 3.23–4.40 (m, 5H), 4.47 (m, 1H), 7.37 (d, 2H, J=10.5 Hz), 7.87 (d, 2H, J=10.5 Hz).

Infrared (film): 2930, 2860, 1600, 1445, 1375, 1175, 905, 815, 670 cm$^{-1}$. TLC (Silica Gel GF): Rf=0.48 in 20% ethyl acetate in hexane.

(f) (1-Tetrahydropyranyloxy-3-iodopropyl)cyclohexane

A solution of 36.74 g (92.65 mmol) of the compound from Example 2(e), 1.5 ml of diisopropylethylamine, 360 ml of acetone and 83.33 g (550 mmol) of sodium iodide was stirred at room temperature under nitrogen for 20 hours. The solution was then cooled using an ice bath and concentrated via rotovap at room temperature to give a red-orange solid which was dissolved in ethyl acetate, washed with 5% aqueous sodium thiosulfate then with brine, dried over anhydrous magnesium sulfate, filtered, and the filtrate concentrated via rotovap at room temperature to give a yellow oil. The oil was chromatographed on silica gel, eluting with ethyl acetate in SSB to give 27.47 g of compound 2(f).

NMR (CDCl$_3$, TMS): δ 0.63–2.53 (m, 19H), 3.07–3.70 (m, 4H), 3.77–4.10 (m, 1H), 4.48–4.82 (m, 1H).

Infrared (film): 2925, 2850, 1450, 1200, 1130, 1115, 1075, 1065, 1035, 1023, 980 cm$^{-1}$. TLC (Silica Gel GF): Rf=0.47 in 10% ethyl acetate in hexane.

(g)

Dimethyl[(4R)-4-cyclohexyl-4-tetrahydropyran-2-yloxybutyl]phosphonate

To 500 ml of dry tetrahydrofuran cooled to −40° C. under nitrogen was added 9.98 ml (96.7 mmol) of diethylamine. The solution was treated with 60 ml (93 mmol) of n-butyllithium (1.55M in hexane) dropwise maintaining the temperature below −30° C. The solution was stirred at −35° C. for 15 minutes then cooled to −75° C. A solution of 10.6 g (85.4 mmol) of dimethylmethyl phosphonate in 50 ml of dry tetrahydrofuran was added dropwise maintaining the temperature below −70° C. The solution was stirred for 30 minutes at −75° C. after which 27.29 g (77.5 mmol) of (1-tetrahydropyranyloxy-3-iodopropyl)cyclohexane in 100 ml of dry tetrahydrofuran was added dropwise maintaining the temperature below −70° C. The reaction mixture was stirred at −70° C. for one hour then allowed to warm to −10° C. over 4 hours. The reaction was quenched with 1:1 brine/water and the layers separated. The aqueous layer was extracted with ethyl acetate. The organic layers were combined, washed with brine, dried over anhydrous sodium sulfate, filtered, and the filtrate concentrated in vacuo. The resulting product was chromatographed on silica gel eluting the product with ethyl acetate to give 18.14 g of compound 2(g).

NMR (CDCl$_3$, TMS): δ 0.63–2.53 (m, 23H), 3.23–4.20 (m, 3H), 3.70 (s, 3H), 3.83 (s, 3H), 4.60 (bs, 1H).

Infrared (film): 2930, 3850, 1450, 1245, 1200, 1130, 1115, 1060, 1030, 990, 835, 815 cm$^{-1}$. TLC (Silica Gel GF): Rf=0.14 in ethyl acetate.

EXAMPLE 3

15-Cyclohexyl-9-deoxy-13,14-dihydro-2',9α-methano-4,5,6,16,17,18,19,20-octanor-3,7-(1',3'-interphenylene)-PGF$_1$ (Formula III)

(a)

15-Cyclohexyl-8,12-didehydro-9,11-dideoxy-13,14-dihydro-2',9-methano-3-oxa-11-oxo-1,4,5,6,16,17,18,19,20-nonanor-3,7-(1',3'-interphenylene)-PGF$_1$, 15-(tetrahydropyranyl ether)

A solution of 14.97 g (42.97) mmol of the product of Example 2 and 424 ml of dry tetrahydrofuran, degassed and flushed with nitrogen, was cooled to −78° C. The stirred solution was treated with 29.03 ml (43.83 mmol) of 1.51M n-butyllithium dropwise over 20 minutes, then stirred for one hour at −78° C. A solution of 4.47 g (20.67 mmol) of 2,3,3A,4-tetrahydro-5-methoxy-2-oxonaphtho[2,3-B]furan (the product of Example 1) in 84 ml of dry tetrahydrofuran, degassed and flushed with nitrogen and cooled to −78° C. under nitrogen, was added via cannula and under nitrogen pressure dropwise over 30 minutes. The resulting solution was stirred for 4 hours while allowing the temperature to rise slowly to −10° C. after which the solution was treated dropwise with 1.23 ml (21.44 mmol) of glacial acetic acid. The reaction mixture was stirred for 15 minutes at ambient temperature and heated at 65° C. for 6 hours. The resulting yellow-green solution was cooled to 5° C., neutralized to about pH 6 with brine containing 1M aqueous hydrochloric acid, and extracted with ethyl acetate. The organic layers were combined and washed with 3:1 brine/saturated aqueous sodium bicarbonate and then with brine and dried over anhydrous sodium sulfate, filtered and concentrated in vacuo. The resulting crude product was chromatographed on silica gel to give 6.45 g (71%) of the title compound 3(a).

NMR (CDCl$_3$, TMS) δ: 0.70–3.00 (m, 25H), 3.20–4.33 (m, including 3H singlet at δ3.83, 9H), 4.50–4.83 (m, 1H), 6.73 (d, 2H, J=7.5 Hz), 7.20 (d of d, 1H, J$_1$=J$_2$=7.5 Hz).

Infrared (mull): 2928, 2852, 1740, 1700, 1653, 1585, 1471, 1451, 1441, 1252, 1371, 1076, 1031, 1024, 998, 772 cm$^{-1}$. TLC (Silica Gel GF) Rf=0.37 in 20% ethyl acetate in hexane.

(b)

15-Cyclohexyl-9,11-dideoxy-13,14-dihydro-2',9α-methano-3-oxa-11-oxo-1,4,5,6,16,17,18,19,20-nonanor-3,7-(1',3'-interphenylene)-12-epi-PGF$_1$, 15-(tetrahydropyranyl ether)

To a solution of 6.45 g of the compound of Example 3(a) in 300 ml of degassed ethanol was added a solution of 2.16 g of 10% palladium on carbon and 0.16 g of anhydrous potassium carbonate. The resulting mixture was hydrogenated at 50 psi for 42 hours after which the mixture was filtered through a pad of 1:1 celite/anhydrous magnesium sulfate. The colorless solution was concentrated in vacuo to give 5.2 g of colorless oil which was filtered through silica gel 60 washing with 20% ethyl acetate in hexane to give 6.45 g of compound 3(b). Rf 0.33 in 20% ethyl acetate in hexane.

(c)

15-Cyclohexyl-9,11-dideoxy-13,14-dihydro-2',9α-methano-3-oxa-11-oxo-1,4,5,6,16,17,18,19,20-nonanor-3,7-(1',3'-interphenylene)-PGF$_1$, 15-(tetrahydropyranyl ether)

To 7.7 g of the compound of Example 3(b) in 615 ml of 95% ethanol was added 130 ml of 10% aqueous sodium hydroxide and the resulting solution was degassed and flushed with nitrogen and heated at reflux for 7.5 hours under nitrogen. The reaction was cooled to room temperature and approximately two-thirds of the solvent was removed in vacuo. The remaining material was diluted with brine and extracted with ethyl acetate. The combined organics were washed with brine, dried over anhydrous sodium sulfate, filtered and concentrated in vacuo. The crude product was flash chromatographed on silica gel to give 6.5 g (84%) of the title compound 3(c).

NMR (CDCl$_3$, TMS) δ: 0.70–3.67 (m, 30H), 3.69–4.23 (m, 6H, including 3H singlet at 3.83δ), 4.50–4.83 (m, 1H), 6.80 (d of d, 2H, J$_1$=J$_2$=7.5 Hz), 7.20 (d of d, 1H, J$_1$=J$_2$=7.5 Hz).

Infrared (mull): 2929, 2868, 2850, 1737, 1588, 1470, 1450, 1443, 1257, 1201, 1133, 1114, 1088, 1077, 1051, 1030, 1025, 995, 766 cm$^{-1}$. TLC (Silica Gel GF): Rf=0.37 in ethyl acetate in hexane.

(d)

15-Cyclohexyl-9-deoxy-13,14-dihydro-2',9α-methano-3-oxa-1,4,5,6,16,17,18,19,20-nonanor-3,7-(1',3'-interphenylene)-PGF$_1$ To 1.66 g (43.68 mmol) of sodium borohydride cooled to −30° C. was slowly added 200 ml of absolute methanol and the resulting suspension was stirred for 10 minutes and treated with a solution of 6.2 g (14.07 mmol) of the compound of Example 3(c) in 9 ml of dry methylene chloride and 45 ml of absolute methanol dropwise maintaining the temperature of the solution at −30° C. The resulting solution was stirred at −30° C. for 4 hours, then at −25° C. for 2.5 hours after which the reaction was quenched with 12.2 ml of glacial acetic acid then diluted with brine and extracted with ethyl acetate. The organic layers were combined and washed with saturated aqueous sodium bicarbonate, then washed with brine, dried over anhydrous sodium sulfate, filtered and concentrated in vacuo to give 6.9 g of a colorless oil [TLC (Silica gel GF; 20% ethyl acetate in hexane): 5 spots with the major spot at Rf=0.17.] The oil was dissolved in 30.2 ml of tetrahydrofuran and diluted with 90.6 ml of glacial acetic acid and 45.3 ml of deionized water, and stirred at 45° C. under nitrogen for 3 hours. The solution was then cooled to room temperature, diluted with brine and extracted with 3:2 ethyl acetate/hexane. The organic layers were combined and washed with brine. All the organic layers were combined, dried over anhydrous sodium sulfate, filtered and concentrated in vacuo using toluene to azeotrope the acetic acid. The resulting colorless oil was chromatographed on silica gel to give 1.7 g of the title compound 3(d).

NMR (CDCl$_3$, TMS) δ: 0.70–3.07 (m, 26H), 3.10 (m, including singlet at 3.83δ, 5H), 6.67–6.97 (m, 2H), 7.13 (d of d, 1H, $J_1=J_2=7.5$ Hz).

Infrared (mull): 3359, 2926, 2852, 1587, 1477, 1472, 1450, 1338, 1326, 1263, 1103, 1077, 1045, 1031, 772, 731, 695 cm$^{-1}$. TLC (Silica Gel GF): Rf 0.26 in 50% ethyl acetate in hexane; Rf=0.28 in 20% acetone/methylene chloride.

(e)

15-Cyclohexyl-9-deoxy-13,14-dihydro-2',9α-methano-3-oxa-1,2,4,5,6,16,17,18,19,20-decanor-3,7-(1',3'-interphenylene)-PGF$_1$ A solution of 70 ml of dry tetrahydrofuran and 2.34 ml of diphenylphosphine, degassed and cooled to 0° C. under nitrogen, was treated with 8.10 ml (12.72 mmol) of n-butyllithium (1.57M in hexane) dropwise over 15 minutes then stirred an additional 30 minutes at ambient temperature after which 1.57 g ( 4.38 mmol) of the compound of Example 3(d) in 13.5 ml of dry tetrahydrofuran was added under nitrogen pressure over 15 minutes. The mixture was heated at reflux for 8 hours under nitrogen, cooled to 0° C. after which 3.25 ml (18.22 mmol) of diphenylphosphine was added, treated with 11.29 ml (17.73 mmol) of n-butyllithium (1.57M in hexane) dropwise over 15 minutes. The solution was stirred at ambient temperature for 30 minutes then refluxed for 16 hours all under nitrogen pressure. The solution was then cooled to 0° C. and poured into ice cold brine containing aqueous hydrochloric acid and extracted with ethyl acetate. The organic layers were combined, washed with brine, dried over anhydrous sodium sulfate, filtered, and concentrated in vacuo. The resulting colorless oil was chromatographed on silica gel 60 eluting with 50% ethyl acetate in hexane to give 1.5 g of the product 3(e).

NMR (CDCl$_3$, TMS) δ: 0.70–3.97 (m, 28H), 6.00–6.60 (m, 1H), 6.63–6.87 (M, 2H), 7.03 (d of d, 1H, $J_1J_2=7.5$ Hz).

Infrared (mull): 3316, 3071, 2954, 2906, 2869, 2851, 1468, 1451, 1376, 1284, 1265, 1063, 1045, 706 cm$^{-1}$.

TLC (Silica Gel GF): Rf=0.16 in 50% ethyl acetate in hexane.

(f)

15-Cyclohexyl-2-decarboxy-2-cyano-9-deoxy-13,14-dihydro-2',9α-methano-3-oxo-4,5,6,16,17,18,19,20-octanor-3,7-(1',3'-interphenylene)-PGF$_1$ The phenol from 3(e) (1.31 g, 15.4 mmol) was combined with 11.26 g (165 mmol) of anhydrous potassium carbonate, 8.79 ml (281 mmol) of chloroacetylnitrile and 40 ml of acetone. The solution was degassed and flushed with nitrogen and refluxed for 44 hours under nitrogen, cooled to 20° C., diluted with 1:1 brine/water and extracted with ethyl acetate. The organic layer was washed with brine, dried over anhydrous sodium sulfate, filtered and concentrated in vacuo. The resulting oil was chromatographed on silica gel 60 eluting with 20% acetone in methylene chloride to give 1.3 g of the product 3(f).

NMR (CDCl$_3$, TMS) δ: 0.70–3.00 (m, 26H), 3.17–3.93 (m, 2H), 4.77 (s, 2H), 6.90 (d of d, 2H, $J_1=J_2=7.5$ Hz), 7.20 (d of d, 1H, $J_1=J_2=7.5$ Hz).

IR (mull): 3330, 2930, 2860, 2240, 1725 (sh), 1685, 1605, 1585, 1445, 1275, 1235, 1175, 1110, 1080, 1025, 975, 890, 775, 705 cm$^{-1}$. TLC (Silica Gel GF): Rf 0.40 in 20% acetone in methylene chloride.

(g) The nitrile from 3(f) (0.97 g, 2.53 mmol) was combined with 19.17 ml of 25% aqueous potassium hydroxide and 57.5 ml of methanol, degassed and flushed with nitrogen. The solution was refluxed for 6 hours, cooled to 0° C., acidified to pH 6 with ice cold aqueous hydrochloric acid in brine, and extracted with ethyl acetate. The combined organic layers were washed with brine, dried over anhydrous sodium sulfate, filtered, and concentrated in vacuo. The resulting solid was chromatographed on CC-4 acid washed silica gel eluting with ethyl acetate in hexane to give 1.06 g of solid which was crystallized from hot tetrahydrofuran and hexane to give 0.589 g of 15-cyclohexyl-9-deoxy-13,14-dihydro-2',9α-methano-3-oxa-4,5,6,16,17,18,19,20-octanor-3,7-(1',3-interphenylene)-PGF$_1$ (m.p. 117°–118° C.).

NMR (CD$_3$)$_2$CO, TMS) δ: 0.70–3.00 (m, 29H), 4.68 (s, 2H), 6.60–6.90 (m, 2H), 7.10 (d of d, 1H; $J_1=J_2=7.5$ Hz).

Infrared (mull): 3380, 2930, 2850, 2750, 1735 (sh), 1710, 1605, 1590, 1455, 1420, 1375, 1260, 1255, 1106, 1085, 1025, 1015, 910, 895, 775, 740 cm$^{-1}$.

FORMULA CHART

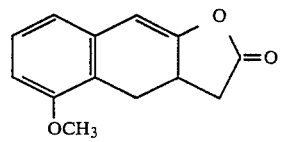

Formula I

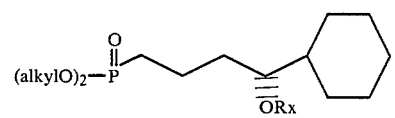

Formula II

-continued
FORMULA CHART
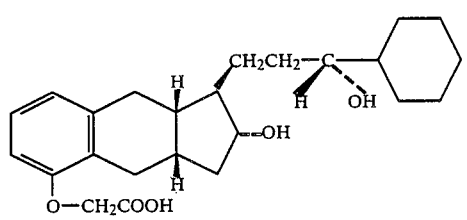
Formula III
We claim:
1. The compound 15-cyclohexyl-9-deoxy-13,14-dihydro-2′,9α-methano-3-oxa-4,5,6,16,17,18,19,20-octanor-3,7(1′,3-interphenylene)PGF$_1$ and pharmacologically acceptable salts thereof.
* * * * *